United States Patent
Saito et al.

[11] Patent Number: 6,144,871
[45] Date of Patent: Nov. 7, 2000

[54] CURRENT DETECTING SENSOR AND METHOD OF FABRICATING THE SAME

[75] Inventors: Soichi Saito; Atsushi Saito, both of Tokyo, Japan

[73] Assignee: NEC Corporation, Tokyo, Japan

[21] Appl. No.: 09/276,936

[22] Filed: Mar. 26, 1999

[30] Foreign Application Priority Data

Mar. 31, 1998 [JP] Japan ................................. 10-086215

[51] Int. Cl.⁷ ........................................................ A61B 5/05
[52] U.S. Cl. ........................... 600/395; 600/396; 600/345
[58] Field of Search ..................................... 600/345, 366, 600/372, 395, 396, 397

[56] References Cited

U.S. PATENT DOCUMENTS

| | | | |
|---|---|---|---|
| 4,571,292 | 2/1986 | Liu et al. | 204/412 |
| 4,805,624 | 2/1989 | Yao et al. | 600/345 |
| 5,063,081 | 11/1991 | Cozzette et al. | 427/2 |
| 5,837,454 | 11/1998 | Cozzette et al. | 435/6 |
| 6,021,339 | 2/2000 | Saito et al. | 600/345 |

FOREIGN PATENT DOCUMENTS 63-139247  6/1988  Japan .
8-193969   7/1996  Japan .

*Primary Examiner*—Cary O'Connor
*Assistant Examiner*—Navin Natnithithadha
*Attorney, Agent, or Firm*—Young & Thompson

[57] ABSTRACT

There is provided a current detecting sensor including (a) an insulating substrate, (b) a first electrode formed on the insulating substrate, the first electrode comprising an electrically conductive electrode and a metal layer formed on the electrically conductive electrode, the metal layer having a smaller area than a area of the electrically conductive electrode, (c) a second electrode formed on the insulating substrate, (d) a third electrode formed on the insulating substrate, (e) an insulating protective film covering the insulating substrate therewith and further covering at least edges of the first, second and third electrodes therewith, the insulating protective film being formed with first, second and third openings at upper surfaces of the first, second and third electrodes, respectively, and (f) an organic film covering the first to third electrodes and the insulating protective film therewith. The current detecting sensor prevents the organic film from being peeled off due to poor coverage over edges of the electrodes, and makes it possible to lengthen a lifetime thereof.

37 Claims, 8 Drawing Sheets

CURRENT DETECTING SENSOR AND METHOD OF FABRICATING THE SAME

BACKGROUND OF THE INVENTION

1. Field of the Invention

The invention relates to a current detecting sensor, and more particularly to a current detecting sensor having three electrodes, applicable to a bio-sensor for measuring urine sugar. The invention relates also to a method of fabricating such a current detecting sensor.

2. Description of the Related Art

Figure 1:
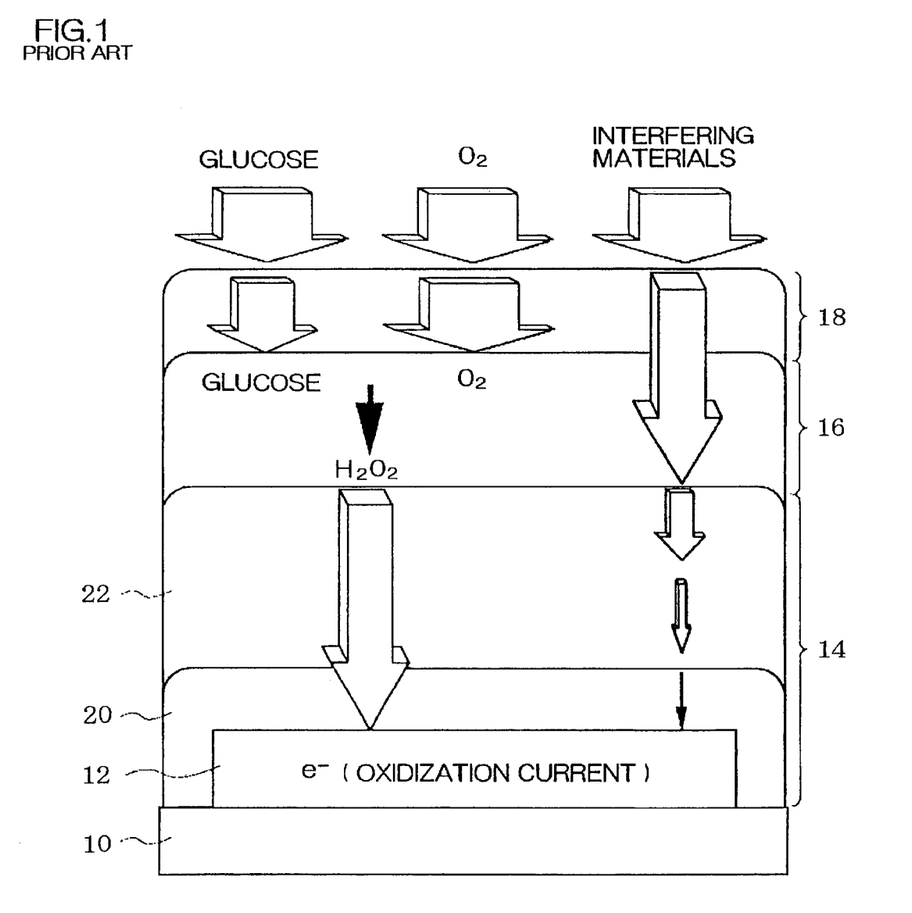
FIG. 1 is a schematic view illustrating a structure of a film constituting a sensitive section of a bio-sensor for measuring urine sugar.

FIG. 1 illustrates a structure of a film constituting a sensitive section of a bio-sensor for measuring urine sugar. The film structure is comprised of a substrate 10, an electrode 12 formed on the substrate 10, and an organic film formed over the electrode 12 and the substrate 10.

The organic film is comprised of a first film 14 formed over the electrode 12 and the substrate 10, a second film 16 formed on the first film 14, and a third film 18 formed on the second film 16.

The third film 18 restricts transmission therethrough of a solution containing a material to be tested in order to ensure certain dynamic range. The second film 16 is a film to which glucose oxidase (GOD) acting as a catalyst is fixed. The first film 14 is a film preventing interfering materials from reaching the electrode 12. The first film 14 is comprised of a coupling material for enhancing adhesion between the first film 14 and the substrate 10, and a selectively transmissive film which does not allow selected interfering materials to pass therethrough.

Figure 2:
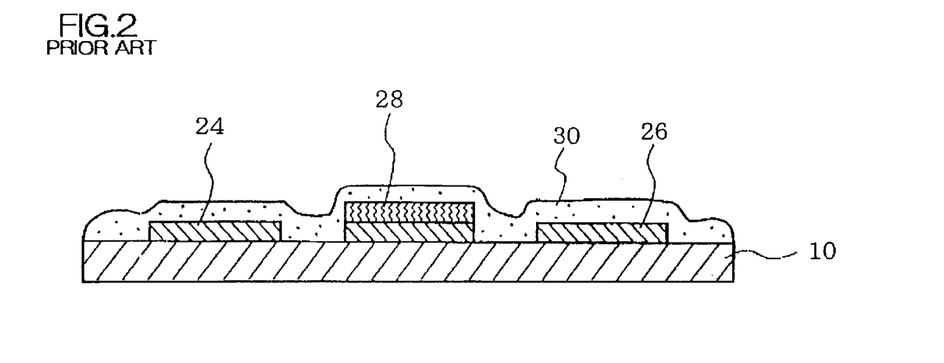
FIG. 2 is a cross-sectional view of a conventional bio-sensor having a three electrodes structure.

The electrode 12 is comprised of an operation electrode 24, an opposing electrode 26, and a reference electrode 28 (see FIG. 2).

In the illustrated film structure, glucose to be measured reacts with enzyme by virtue of catalytic action of glucose oxidase in the second film 16, and as a result, there is generated hydrogen peroxide ($H_2O_2$). The thus generated hydrogen peroxide is oxidized in the operation electrode 24 with the result of generation of oxidation current. The thus generated oxidation current is detected between the operation current 24 and an opposing electrode 26.

Glucose oxidase makes reaction in accordance with the following reaction formula (A).

Glucose+$O_2$→Gluconic acid+$H_2O_2$  (A)

The following reactions are made in the operation electrode 24 and the opposing electrode 26, respectively.

$H_2O_2$→$2H^+$+$O_2$+$2e-$  (B)

$2H^+$+$O_2/2$+$2e-$→$H_2O$  (C)

The following reaction is made in an entire electrode system including the operation electrode 24 and the opposing electrode 26.

$H_2O_2$→$H_2O$+$O_2/2$  (D)

When a reaction in the bio-sensor comes to an equilibrium state, a glucose concentration at time T can be measured, based on an amount of electrons (e−) in the above-mentioned reaction formulas, to flow into the electrode 12 per a unit time, which amount indicates a current generated at time T.

When hydrogen peroxide as an intermediate product is made to react on the electrode, it is necessary to apply a predetermined voltage across the operation electrode and the opposing electrode through a solution. However, there is generated a voltage drop in dependence on quality of a solution, and hence, a difference is made between a target voltage and an actual voltage. In order to prevent generation of such a difference, the bio-sensor is usually designed to include a reference electrode, which cooperates with the other two electrodes, namely, the operation electrode and the opposing electrode, to define a three electrodes structure.

In the bio-sensor having a three electrodes structure, a material of which a reference electrode is composed is required to have the following characteristics.

1. A reference electrode is difficult to be solved, and an oxidation film is unlikely to be generated.

2. A wide range of voltages can be checked without being interfered by a reaction to be made by a reference electrode itself.

3. Solvent and support salts are unlikely to be decomposed by a metal of which a reference electrode is composed.

4. It is possible to readily make a clean surface.

In order to meet with the above-mentioned requirements, a reference electrode may be composed of Pt, Au, Pd or C. If a reference electrode is used for detecting hydrogen peroxide, it would be important that a voltage at which hydrogen peroxide is detected is as small as possible, that a material of which a reference material is composed is not fused at the above-mentioned voltage, that a material of which a reference electrode is composed is unlikely to react with components basically contained in a solution, such as water and salts, namely, a base current is small, and that there is obtained high sensitivity for detection of hydrogen peroxide. Taking those into consideration, it is considered that Pt is best as a material of which a reference electrode is composed.

Platinum (Pt) has higher sensitivity to hydrogen peroxide by an order than that of gold (Au), and a voltage to be applied to a reference electrode composed of platinum is lower than a voltage to be applied to a reference electrode composed of gold. In addition, platinum has an advantage that it is less influenced by a substance such as ascorbic acid, which would be an interfering substance when urine is tested.

A current runs through an opposing electrode in a direction opposite to a direction in which a current runs through an operation electrode. Hence, an opposing electrode is composed of preferably of a material which has a small resistance, and which is not polarized under conditions for measuring hydrogen peroxide. In general, an opposing electrode is composed of the same material as a material of which an operation electrode is composed. That is, an opposing electrode is usually composed of platinum.

Both operation and opposing electrodes are formed on a substrate with a titanium layer being sandwiched therebetween, because a titanium layer has high adhesion with a substrate.

As mentioned earlier, a voltage of a reference electrode is determined in dependence on a reference electrode, and thus, a reference electrode is required to have the following characteristics.

1. A reaction which occurs at a surface of a reference electrode is a reversible one, and such a reaction responds to certain chemical species in accordance with Nernst's equilibrium potential equation.

2. A potential of a reference electrode is stable in spite of the lapse of time.

3. A potential of a reference electrode would quickly returns to an initial potential, even if a small current runs therethrough.

4. Even if a temperature varies, a reference electrode would have a fixed potential when a temperature varied to a certain temperature.

For instance, a reference electrode may be formed as a hydrogen electrode, a calomel electrode or an Ag/AgCl electrode. A reference electrode is usually formed as an Ag/AgCl electrode, because it can be readily fabricated, it has superior stability, and it can be handled with ease.

FIG. 2 is a cross-sectional view of a conventional sensor having a three electrodes structure. The illustrated sensor is comprised of an insulating substrate 10 composed of a material such as quartz and ceramic, an operation electrode 24 formed on the insulating substrate 10, an opposing electrode 26 formed on the insulating substrate 10, a reference electrode 28 formed on the insulating substrate 10 between the operation electrode 24 and the opposing electrode 26, and an organic film 30 covering the insulating substrate 10 and the electrodes 24, 26 and 30 therewith. The operation electrode 24 is comprised of a platinum layer and a titanium layer. The reference electrode 28 is comprised of a silver layer, a silver chloride layer, a platinum layer, and a titanium layer.

In the conventional sensor illustrated in FIG. 2, the silver chloride layer is gradually fused from an upper surface thereof in a thickness-wise direction while the sensor is in operation. Hence, there is generated a cavity in the reference electrode 28, resulting in that the organic film 30 is peeled off, and as an alternative, the organic film 30 is wrinkled. If the organic film 30 were peeled off because of a cavity having been generated in the reference electrode 28, the reference electrode 24 and the opposing electrode 26 are also influenced by the reference electrode 28 being peeled off.

The organic film 30 is deposited over the substrate 10 by spin coating. Since the organic film 30 is thin, the organic film 30 has poor coverage over edges of the electrodes 24, 26 and 28, and hence, is often cracked above the edges, resulting in that the organic film 30 begins to be peeled off from such a crack.

Figure 3A:
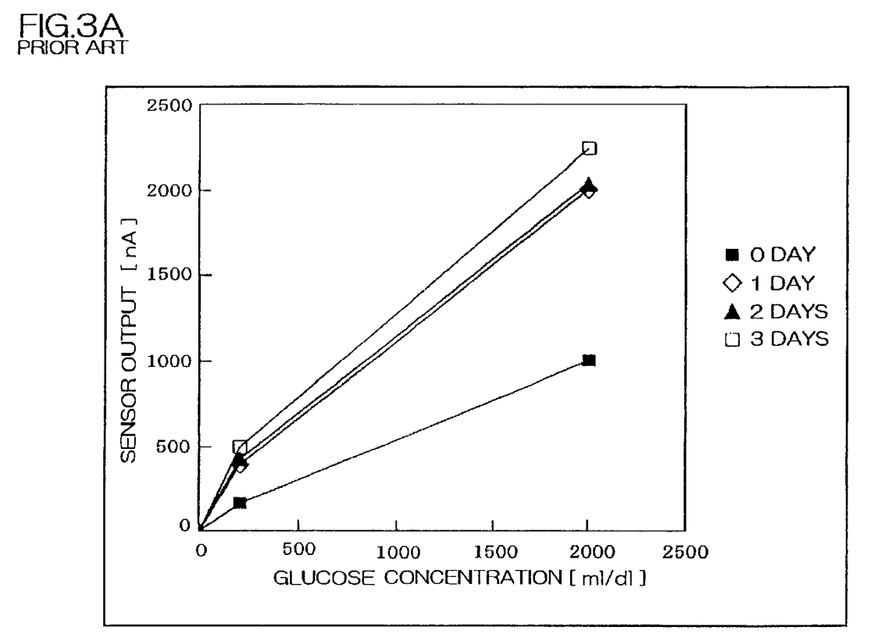
FIG. 3A illustrates a relation between a sensor output and a glucose concentration in a sensor having stable sensitivity.
Figure 3B:
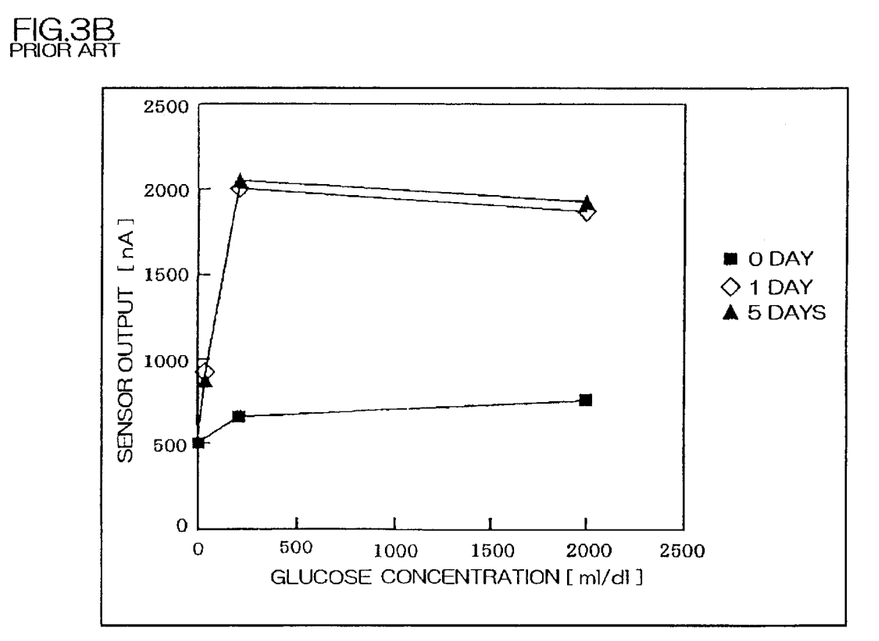
FIG. 3B illustrates a relation between a sensor output and a glucose concentration in a sensor having unstable sensitivity.

If the organic film 30 is peeled off due to fusion of the silver chloride film and poor coverage above the edges of the electrodes, sensitivity or response characteristic of the sensor would be degraded. FIG. 3A illustrates a relation between a sensor output and a glucose concentration in a sensor having stable sensitivity, whereas FIG. 3B illustrates the same in a sensor having unstable sensitivity. As illustrated in FIG. 3B, if sensitivity is unstable, a sensor output would be saturated at a low glucose concentration, resulting in that there cannot be obtained desired dynamic range.

In the conventional sensor, the silver chloride film constituting the reference electrode 28 is fused in a thickness-wise direction. The silver chloride film is usually designed to have a small thickness, specifically a thickness equal to or smaller than 1 µm. A lifetime of the sensor terminates when the silver chloride film is all fused. Hence, the conventional sensor is accompanied with a problem of a short lifetime.

In addition, the reference electrode 28 is required to have a stable self-potential. However, the silver chloride film, the silver film, the platinum film and the titanium film are all exposed at a sidewall of the reference electrode 28, and hence, the unnecessary metal films, namely the silver film, the platinum film and the titanium film, prevent a self-potential from being stabilized.

SUMMARY OF THE INVENTION

In view of the above-mentioned problems, it is an object of the present invention to provide a current detecting sensor which is capable of preventing peel-off of an organic film which is caused by fusion of a silver chloride film and poor coverage above edges of electrodes.

It is also an object of the present invention to provide a current detecting sensor having a longer lifetime than a lifetime of a conventional sensor.

Another object of the present invention is to provide a current detecting sensor which is capable of stabilizing a self-potential of a reference electrode.

A further object of the present invention is to provide a method of fabricating such a current detecting sensor.

In one aspect of the present invention, there is provided a current detecting sensor including (a) an insulating substrate, (b) a first electrode formed on the insulating substrate, the first electrode comprising an electrically conductive electrode and a metal layer formed on the electrically conductive electrode, the metal layer having a smaller area than a area of the electrically conductive electrode, (c) a second electrode formed on the insulating substrate, (d) a third electrode formed on the insulating substrate, (e) an insulating protective film covering the insulating substrate therewith and further covering at least edges of the first, second and third electrodes therewith, the insulating protective film being formed with first, second and third openings at upper surfaces of the first, second and third electrodes, respectively, and (f) an organic film covering the first to third electrodes and the insulating protective film therewith.

It is preferable that the metal layer has a two-layered structure. For instance, the two-layered structure may include a silver (Ag) layer and a silver chloride (AgCl) layer formed on the silver layer.

It is also preferable that the electrically conductive electrode has a multi-layered structure. For instance, the multi-layered structure may include a platinum (Pt) layer and a titanium (Ti) layer formed on the platinum layer. As an alternative, the multi-layered structure may include a silver (Ag) layer, a platinum (Pt) layer, and a titanium (Ti) layer deposited in this order.

It is preferable that the first opening has a smaller diameter than diameters of the second and third openings. For instance, the first opening may have a diameter in the range of 1 µm to 500 µm both inclusive.

It is preferable that the insulating protective film has a thickness equal to or greater than thicknesses of the first, second and third electrodes.

For instance, the insulating protective film may be in the form of a mesh, in which case, the second and third openings are comprised of a plurality of fine openings.

The insulating substrate may be composed of a material selected from a group consisting of glass, ceramic, polyimide and glass epoxy, and the insulating protective film may be composed of a material selected from a group consisting of photoresist, polyimide resin, solder resist, epoxy resin, phenol resin, silicon dioxide, and glass.

The organic film may be comprised of a first film for restricting transmission of a solution containing a material to be tested, therethrough, a second film to which enzyme is fixated, and a third film for removing an interfering material contained in the solution.

For instance, the first film may be composed of a material selected from a group consisting of perfluorocarbon and silicone, the second film may be composed of a mixture of glucose oxidase (GOD), bull serum albumin (BSA), and glutaric aldehyde (GA), and the third film may be composed of γ-aminopropyltrietoxysilane and ionomer fluoride.

There is further provided a current detecting sensor including (a) an insulating substrate, (b) a first electrode formed on the insulating substrate, the first electrode comprising an electrically conductive electrode and a plurality of metal islands formed on the electrically conductive electrode, the metal islands each having a smaller area than a area of the electrically conductive electrode, (c) a second electrode formed on the insulating substrate, the second electrode surrounding the first electrode therewith, (d) a third electrode formed on the insulating substrate, (e) an insulating protective film covering the insulating substrate therewith and further covering at least edges of the first, second and third electrodes therewith, the insulating protective film being formed with first, second and third openings at upper surfaces of the first, second and third electrodes, respectively, and (f) an organic film covering the first to third electrodes and the insulating protective film therewith.

It is preferable that the third electrode surrounds the second electrode therewith.

In another aspect of the present invention, there is provided a method of fabricating a current detecting sensor, comprising the steps of (a) forming first to third electrodes on a substrate, the first electrode being comprised of an electrically conductive electrode and a metal layer formed on the electrically conductive electrode, the metal layer having a smaller area than a area of the electrically conductive electrode, the second electrode being comprised of an electrically conductive electrode, the third electrode being comprised of an electrically conductive electrode, (b) depositing an insulating protective film over a product resulting from the step (a), (c) patterning the insulating protective film in such a manner that the insulating protective film covers the substrate therewith and further covers at least edges of the first, second and third electrodes therewith, and that the insulating protective film has first, second and third openings at upper surfaces of the first, second and third electrodes, respectively, and (d) covering a product resulting from the step (c) with an organic film.

It is preferable that the metal layer is comprised of a silver (Ag) layer and a silver chloride (AgCl) layer formed on the silver layer, in which case, the method may further include the step of chlorinating the silver layer to thereby turn the silver layer at a surface thereof into the silver chloride layer.

It is preferable that the first opening is formed in the step (c) so as to have a smaller diameter than diameters of the second and third openings.

It is also preferable that the insulating protective film is patterned in the step (c) into a mesh, and the second and third openings are formed of a plurality of fine openings.

It is preferable that the insulating protective film is deposited in the step (b) in such a manner that the insulating protective film has a thickness equal to or greater than thicknesses of the first, second and third electrodes.

There is further provided a method of fabricating a current detecting sensor, including the steps of (a) forming first to third electrodes on a substrate, the first electrode being comprised of an electrically conductive electrode and a plurality of metal islands formed on the electrically conductive electrode, the metal islands each having a smaller area than a area of the electrically conductive electrode, the second electrode being comprised of an electrically conductive electrode, the third electrode being comprised of an electrically conductive electrode, the second electrode surrounding the first electrode therewith, (b) depositing an insulating protective film over a product resulting from the step (a), (c) patterning the insulating protective film in such a manner that the insulating protective film covers the substrate therewith and further covers at least edges of the first, second and third electrodes therewith, and that the insulating protective film has first, second and third openings at upper surfaces of the first, second and third electrodes, respectively, and (d) covering a product resulting from the step (c) with an organic film.

In the current detecting sensor in accordance with the present invention, the silver chloride layer of the first or reference electrode makes contact with the organic film through the first opening formed through the insulating protective film. While the current detecting sensor is in operation, the silver chloride layer begins to be fused at a portion around the first opening in a thickness-wise direction, and then, is fused in a plane-wise direction.

Though there is generated a cavity after the silver chloride layer has been fused, the organic film is never peeled off, because the insulating protective film acts as a supporting beam, and hence, supports the organic film. Hence, the insulating protective film above a cavity is required to have a strength sufficient to act as a beam and support the organic film, when the silver chloride film is fused in a plane-wise direction. To this end, it is necessary for the silver chloride film to have a size in a plane which is not so greater relative to a size of the first opening. For instance, when the silver chloride layer is formed in a circle, the silver chloride layer is necessary to have a diameter which is not so great relative to a diameter of the first opening. For instance, when the first opening has a diameter of 50 $\mu$m, it is preferable for the silver chloride layer to have a diameter of 0.1 mm.

Since edges of the first to third electrodes are entirely covered with the insulating protective film, it is possible to prevent the organic film from being cracked, when the organic film is formed by spin coating.

In addition, since sidewalls of the silver chloride layer and the underlying electrically conductive electrode both cooperating with each other to thereby constitute the first electrode are covered with the insulating protective film, the first or reference electrode could have a stable self-potential.

Japanese Unexamined Patent Publication No. 8-193969 based on U.S. patent application Ser. No. 266,824 filed on Jun. 27, 1994, has suggested an electrically chemical sensor having operation and reference electrodes both of which are covered only at sidewalls thereof with an insulating film. However, the suggested insulating film is formed only for the purpose of electrically isolating a region other than regions acting as an electrode composed of an electrically conductive material.

Japanese Unexamined Patent Publication No. 63-139247 has also suggested an insulating film similar to the above-mentioned insulating film.

The insulating films suggested in the above-mentioned Publications are quite different in function from the insulating protective film in the present invention. That is, the insulating films disclosed in the above-mentioned Publications are formed for the purpose of defining an effective region acting as an electrode making contact with a solution, and not for the purpose of covering edges of electrodes. In addition, the insulating films disclosed in the abovementioned Publications are formed with any openings.

In addition, in accordance with the present invention, since the insulating protective film is firmly fixed on the electrodes, the organic film is never broken even at a cavity on which an outer pressure acts. To the contrary, in the above-mentioned Publications, since a reference electrode is covered only at a sidewall thereof with the insulating film, the reference electrode will be fused entirely at an exposed surface thereof. In addition, the organic film will be wholly peeled off.

In accordance with the present invention, since the insulating protective film covers the first to third electrodes therewith at their edges, even if a defect were generated in the organic film above the first electrode, and gradually spread towards the second and third electrodes, it would be possible to prevent the defect from further spreading.

In an embodiment of the present invention, the second and third electrodes are covered only at edges thereof with the insulating protective film. That is, the second and third electrodes are exposed to the organic film at most of upper surfaces thereof. As an alternative, the second and third electrodes may be covered at upper surfaces thereof with a mesh-shaped insulating protective film. Even if a defect spreads from the first electrode towards the second and third electrodes, or even if the second and/or third electrodes originally contain(s) a defect, such a mesh-shaped insulating protective film could prevent the defect from further spreading.

In the specification, the insulating protective film in the form of a mesh means an insulating film regularly or irregularly formed with a lot of fine openings. The openings may be a circle, an oval, a triangle, a polygon or any other shapes.

The above and other objects and advantageous features of the present invention will be made apparent from the following description made with reference to the accompanying drawings, in which like reference characters designate the same or similar parts throughout the drawings.

DESCRIPTION OF THE PREFERRED EMBODIMENTS

Figure 4:
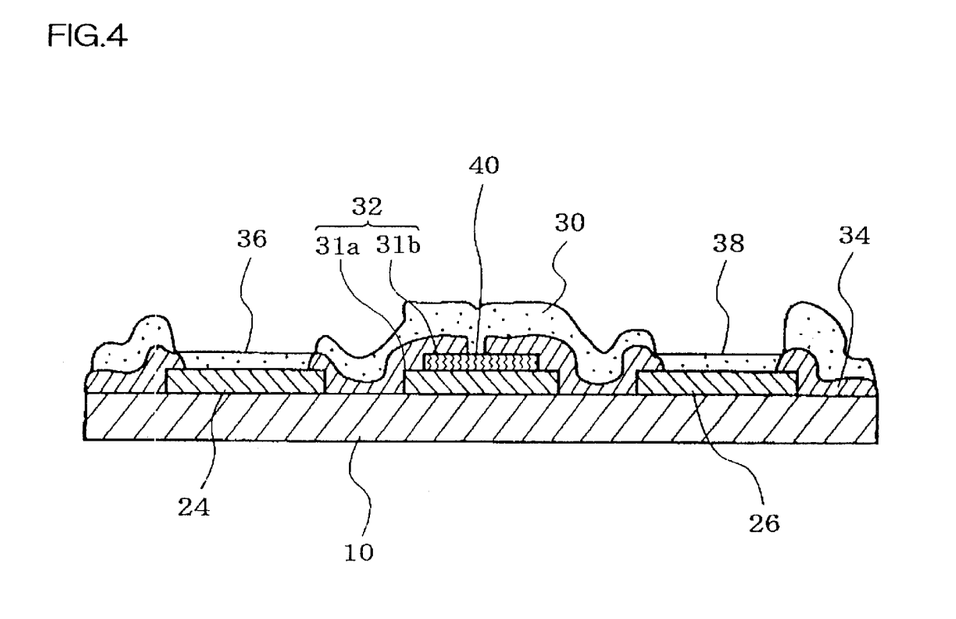
FIG. 4 is a schematic view illustrating a structure of a film constituting a sensitive section of a current detecting sensor in accordance with the first embodiment of the present invention.

FIG. 4 illustrates a structure of a sensitive section of a current detecting sensor in accordance with the first embodiment. The current detecting sensor is applied to a bio-sensor for measuring urine sugar.

The illustrated current detecting sensor is comprised of an insulating substrate 10, an operation electrode 24 formed on the insulating substrate, a reference electrode 32 formed on the insulating substrate 10, an opposing electrode 26 formed on the insulating substrate 10, an insulating protective film 34 covering the insulating substrate therewith and further at least partially covering the operation, reference and opposing electrodes 24, 32 and 26 therewith, and an organic film 30 covering exposed surfaces of the operation, reference and opposing electrodes 24, 32 and 26 and the insulating protective film 34 therewith.

The reference electrode 32 is comprised of an electrically conductive electrode 31a and a two-layered metal layer 31b formed on the electrically conductive electrode 31a.

The electrically conductive electrode 31a has a multi-layered structure. In the instant embodiment, the electrically conductive electrode 31a is comprised of a platinum (Pt) layer and a titanium (Ti) layer formed on the platinum layer.

The metal layer 31b is designed to have a smaller area than a area of the electrically conductive electrode 31a. The two-layered metal layer 31b includes a silver (Ag) layer and a silver chloride (AgCl) layer formed on the silver layer.

The insulating protective film 34 is formed with first, second and third openings 36, 40 and 38 at upper surfaces of the operation, reference and opposing electrodes 24, 32 and 26, respectively. As illustrated in FIG. 4, the first and third openings 36 and 38 are large enough to expose most of upper surfaces of the operation and opposing electrodes 24 and 26. The second opening 40 is in the form of a through-hole. Specifically, the second opening 40 is designed to have a smaller diameter than diameters of the first and third openings 36 and 38.

Thus, the insulating protective film 34 covers edges of the operation, reference and opposing electrodes 24, 32 and 26 therewith. Specifically, the insulating protective film 34 entirely covers sidewalls of the operation electrode 24, the electrically conductive electrode 31a, the metal layer 31b, and the opposing electrode 26 therewith, and further covers a marginal area of upper surfaces of the operation electrode 24 and the opposing electrode 26, an exposed surface of the electrically conductive electrode 31a, and most of an upper surface of the metal layer 31b.

Similarly to the organic film illustrated in FIGS. 1 and 2, the organic film 30 is comprised of a first film, a second film 16, and a third film 18 deposited in this order. The third film restricts transmission therethrough of a solution containing a material to be tested in order to ensure certain dynamic range. The second film is a film to which glucose oxidase (GOD) acting as a catalyst is fixed. The first film is a film preventing interfering materials from reaching the electrodes 24, 32 and 26.

In the instant embodiment, the second opening 40 has a circular cross-section having a diameter in the range of 1 $\mu$m to 500 $\mu$m. The second opening 40 is designed to have such a diameter that a solution can permeate through the organic film 30 in the second opening or through-hole 40. It is preferable that the second opening 40 has a diameter which is as small as possible, in order to narrow a cavity which would be generated when the silver chloride layer.

The thicknesses of those layers are determined in dependence on a resistance to pressure exerted by the insulating protective layer 34 and the organic layer 30, an electrical conductivity, stability as a film, productivity, fabrication cost, and so on. In the instant embodiment, the silver chloride layer, the silver layer, the platinum layer, and the titanium layer are designed to have thicknesses of 2000, 1000, 1000 and 500 angstroms, respectively. The silver chloride layer, the platinum layer, and the titanium layer are designed to have a thickness enough to constitute an electrical conductor.

In the above-mentioned conventional sensor, the silver chloride layer was required to have a thickness as thick as possible for lengthening a lifetime of the sensor. To the contrary, the silver chloride layer is fused in a plane-wise direction thereof in the instant embodiment, the silver chloride layer in the instant embodiment can have a smaller thickness than a thickness of the silver chloride layer in the conventional sensor.

The insulating protective film 34 is designed to have a greater thickness than thicknesses of the operation, reference and opposing electrodes 24, 32 and 26. In the instant embodiment, the insulating protective film 34 has a thickness of about 2 $\mu$m.

Hereinbelow are explained materials of which the above-mentioned elements constituting the current detecting sensor in accordance with the first embodiment are composed.

(A) Insulating substrate 10

The insulating substrate 10 on which the sensitive section of the current detecting sensor is in the form of a planar insulator, and is composed of a material having physical characteristics resistant to a step of patterning a film into an electrode. From this point of view, the insulating substrate 10 may be composed of glass, ceramic, polyimide or glass epoxy.

The insulating substrate 10 has to have a resistance to chemicals and heat, and be planar, because the insulating substrate 10 is subject to a step of being heated in vacuum for making a film of which electrodes will be formed, such as sputtering and evaporation, and a step of photolithography and etching for patterning the film.

The insulating substrate 10 has a thickness which is determined in accordance with how the insulating substrate 10 is mounted on other part.

After the thin organic film 30 has been deposited on the insulating substrate 10, the insulating substrate 10 is separated into chips. Hence, the insulating substrate 10 has to have flatness equal to or smaller than 1 $\mu$m, and be readily separated into pieces. As an example, there may be used a non-alkaline glass substrate as the insulating substrate 10, which is commercially available from NEC Glass, Co. in the tradename of "OA-2". This non-alkaline glass substrate can be readily scribed and broken after the organic film 30 has been deposited thereon.

(B) Operation electrode 24 and Opposing electrode 26

Though platinum is a noble metal and hence expensive, since there are no electrically conductive materials which are chemically stable, the operation and opposing electrodes 24 and 26 are preferably composed of platinum. However, since platinum alone does not have sufficient adhesion to the insulating substrate 10, a titanium film has to be sandwiched between the insulating substrate 10 and the platinum film. The platinum and titanium films can be readily formed on the insulating substrate 10 by sputtering or evaporation.

It is generally difficult to pattern a platinum film by wet etching, and hence, a platinum film is patterned by dry etching, ion milling or a metal mask. A titanium film can be readily patterned by wet etching or dry etching.

Thicknesses of the platinum and titanium films are determined taking many factors into consideration, such as a resistance of a wiring, diffusion of platinum and titanium, purity at a surface of a platinum film, and adhesion of platinum and titanium films. In the instant embodiment, the titanium and platinum films are designed to have thicknesses of 500 and 1000 angstroms, respectively.

(C) Reference electrode 32

Though silver is a noble metal and hence is expensive, silver is most suitable as base metal of which an electrochemically stable reference electrode is composed, because the reference electrode 32 can be readily formed of a thin silver film.

In fabrication of the reference electrode 32, a titanium film, a platinum film, and a silver film are successively deposited on the insulating substrate 10 in this order. Then, the silver film is chlorinated to thereby turn silver into silver chloride. The reference electrode 32 composed of silver chloride can be readily fabricated, and provides a stable self-potential.

The silver film is designed to have a greater thickness than a thickness of the platinum film, because the silver film is subject to the chlorination step. In the instant embodiment, the silver film prior to the chlorination step has a thickness of 2000 angstroms.

(D) Insulating protective film 34

The insulating protective film 34 can be patterned by spin coating an organic material such as photoresist, polyimide resin, solder resist, epoxy resin, and phenol resin, and carrying out photolithography and etching steps. The insulating protective film 34 can be patterned also by screen printing or offset printing. As an alternative, the insulating protective film 34 may be composed of silicon dioxide or glass, and may be patterned by photolithography and etching steps.

(E) First film

As mentioned earlier, the first film 14 is comprised of a coupling material for enhancing adhesion between the first film and the substrate 10, and a selectively transmissive film which does not allow selected interfering materials to pass therethrough. Since a coupling material is deposited also on the platinum electrode and the silver chloride electrode, a coupling material to be used has to have a function of preventing predetermined interfering materials from passing therethrough.

A coupling material can be formed as a film by spin coating. For instance, there may be selected of $\gamma$-aminopropyltriethoxysilane ($\gamma$-APTES) as a coupling material. For instance, a coupling material can be formed by dropping about 1 ml of 1% APTES solution onto the insulating substrate 10, spinning the insulating substrate 10, and heating the insulating substrate 10, if necessary.

Urine usually contains ascorbic acid contained in vitamin drinks, and acetoaminophen contained in a cold remedy, as interfering materials. It is necessary to suppress sensitivity of the current detecting sensor against those materials. For this purpose, the selectively transmissive film comprising a urea film and a Nafion film are electrically, successively deposited on the platinum electrode and the silver chloride electrode. Herein, "Nafion" is a tradename of all ionomer fluoride commercially available from DuPont. These films allow hydrogen peroxide generated in glucose reaction, to pass therethrough, but disallow the above-mentioned interfering materials to pass therethrough.

The selectively transmissive film is necessary to be designed to have sensitivity to glucose equal to or smaller than 5 mg/dl, when a solution contains ascorbic acid and acetoaminophen at 100 mg/dl.

A urea film can be made by carrying out electrochemical treatment in 150 mM NaCl solution containing urea by 40 g/dl. A voltage of 0.7 V relative to a voltage to be applied to the reference voltage 32 is applied to the operation electrode 24 and the opposing electrode 26 for 10 minutes.

A Nafion film can be formed by spin coating 5% Nafion solution on a urea film. The 5% Nafion solution can be almost uniformly applied onto the urea film. Since the Nafion film expands to a little degree on making contact with water, can be smoothly applied, and is hard, it hardly damages the enzyme film and the third film to be formed on the Nafion film. After application of Nafion, a selectively transmissive film stands in a condition determined for stabilization thereof.

(F) Second film

Glucose in urine reacts with an enzyme (GOD) to thereby generate gluconic acid and hydrogen peroxide. An amount of the thus generated hydrogen peroxide is measured in equivalence of a glucose concentration. Hence, sensitivity of the current detecting device is dependent on performances of the second film or enzyme film.

There is prepared in advance a mixture of GOD, BSA, TES and pH adjuster including NaCl, NaOH and HCl solutions. Immediately before spin coating, glutaric aldehyde (GA) as a cross-linking agent is further added to the mixture, and then, the mixture is applied to a film as soon as possible. At this time, since cross-linking reaction has already started, it is necessary to keep a film to which the mixture has been applied, at 4 degrees centigrade or smaller for suppressing cross-linking reaction.

Spin coating characteristic is dependent on a degree to which cross-linking reaction is making progress. The above-mentioned mixture is prepared in such a manner that BSA:GOD:GA is equal to 15:3:2, for instance. The mixture is dropped onto a substrate by about 2 ml. Thereafter, the substrate stands in a condition where an enzyme is not deactivated, in order to stabilize the enzyme.

(G) Third film

As mentioned earlier, the third film restricts transmission therethrough of a solution containing a material to be tested. In order to ensure certain dynamic range of a response characteristic, the third film is formed as an outermost layer of the current detecting sensor. The third film is designed to be composed of water repellent material in order to make it possible to readily wash the current detecting sensor after each measurement.

The third film is designed to have such a thickness that there can be obtained linear concentration characteristic at a concentration in the range of 0 to 2000 mg/dl. Spin conditions are determined in dependence on the thus determined thickness.

For instance, the third film can be made by spin coating perfluorocarbon or silicone onto a surface of the sensor. Thereafter, the sensor stands for stabilizing the thus applied perfluorocarbon or silicone.

Steps of fabricating the electrodes 24, 26 and 32 and the organic film 30 are explained hereinbelow with reference to FIGS. 5 and 6.

Figure 5:
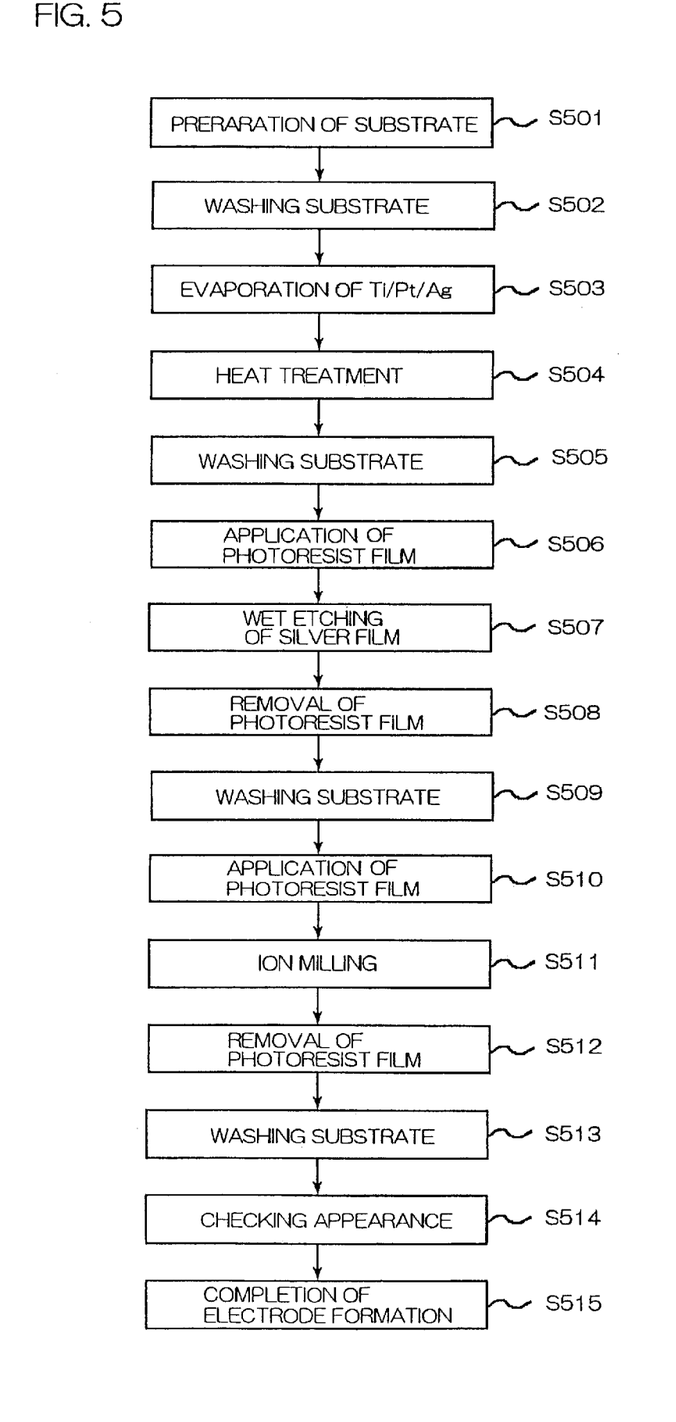
FIG. 5 is a flow chart showing respective steps of a method of fabricating an electrode.

FIG. 5 is a flow chart illustrating respective steps of fabricating the electrodes 24, 26 and 32. In the steps illustrated in FIG. 5, a titanium film, a platinum film, and a silver film are deposited on the insulating substrate 10, and patterned.

First, the insulating substrate 10 is prepared in step 501, and washed in step 502. Then, a titanium film, a platinum film, and a silver film are successively formed on the insulating substrate 10 by evaporation or sputtering in step 503. In order to carry out sputtering, it would be necessary to prepare a target and an apparatus equipped with multi-target. A conventional evaporation apparatus could be used for deposition of the above-mentioned films by evaporation. In addition, evaporation generally provides a qualified film.

Evaporation is carried out heating the insulating substrate 10 at 150 degrees centigrade in step 504 while the films are being formed, in order to enhance adhesion between the films and the insulating substrate 10. Thicknesses of the films are observed through a monitor while being formed, and evaporation is ceased when thicknesses of the films reach target thicknesses.

For instance, target thicknesses of the silver, platinum and titanium films are about 2000, 1000 and 500 angstroms, respectively. The target thicknesses are selected so as to prevent the films from being peeled off by depositing the films to a degree more than needed.

Then, the insulating substrate 10 is washed again in step 505.

Then, a photoresist film is applied on the films in step 506 prior to patterning the Ag/Pt/Ti films. The photoresist film is applied onto the films by spin coating. A thickness of the photoresist film is adjusted by controlling a revolution per minute and coating time. After application of the photoresist film, the photoresist film is pre-baked in a predetermined condition to thereby be cured.

Then, the photoresist film is exposed to light, developed, and post-baked. The platinum and titanium films and silver, platinum and titanium films are patterned in accordance with each of photo mask patterns used in this step.

Though the titanium and silver films can be readily wet etched, it is difficult to wet etch the platinum film. Accordingly, the platinum film is patterned by ion milling.

The silver film is first wet etched in step 507 to thereby be patterned in a condition in which an etchant, temperature, and etching time are optimized.

After the silver film has been patterned, the photoresist film remains unremoved on the platinum and titanium films, and the platinum and titanium films are patterned by dry etching. Since the photoresist film still remains on the substrate, dry etching is carried out with the substrate being cooled by water for preventing a substrate temperature from raising. A patterning accuracy is controlled by varying a high frequency power to be applied, milling time, vacuum degree, and so on.

After the platinum and titanium films have been patterned, the photoresist film is removed in step 508. Then, the substrate is washed in step 509.

Then, a photoresist film is applied again onto the substrate in step 510. Then, the platinum film is patterned by ion milling in step 511. Thereafter, the photoresist film is removed in step 512, and then, the substrate is washed in step 513.

Then, products are checked as to an appearance thereof in step 514. Thus, there is completed the electrodes 24, 32 and 26 in step 515.

The silver film constituting the reference electrode 32 is designed to have a pattern sufficiently smaller than a pattern of the underlying platinum film. For instance, if the platinum pattern has a diameter of 1 mm, the silver pattern would be designed to have a diameter of about 0.1 mm. The silver pattern is formed by the number of one or greater. The silver pattern will make a silver chloride island on a platinum electrode in a later mentioned step.

Figure 6:
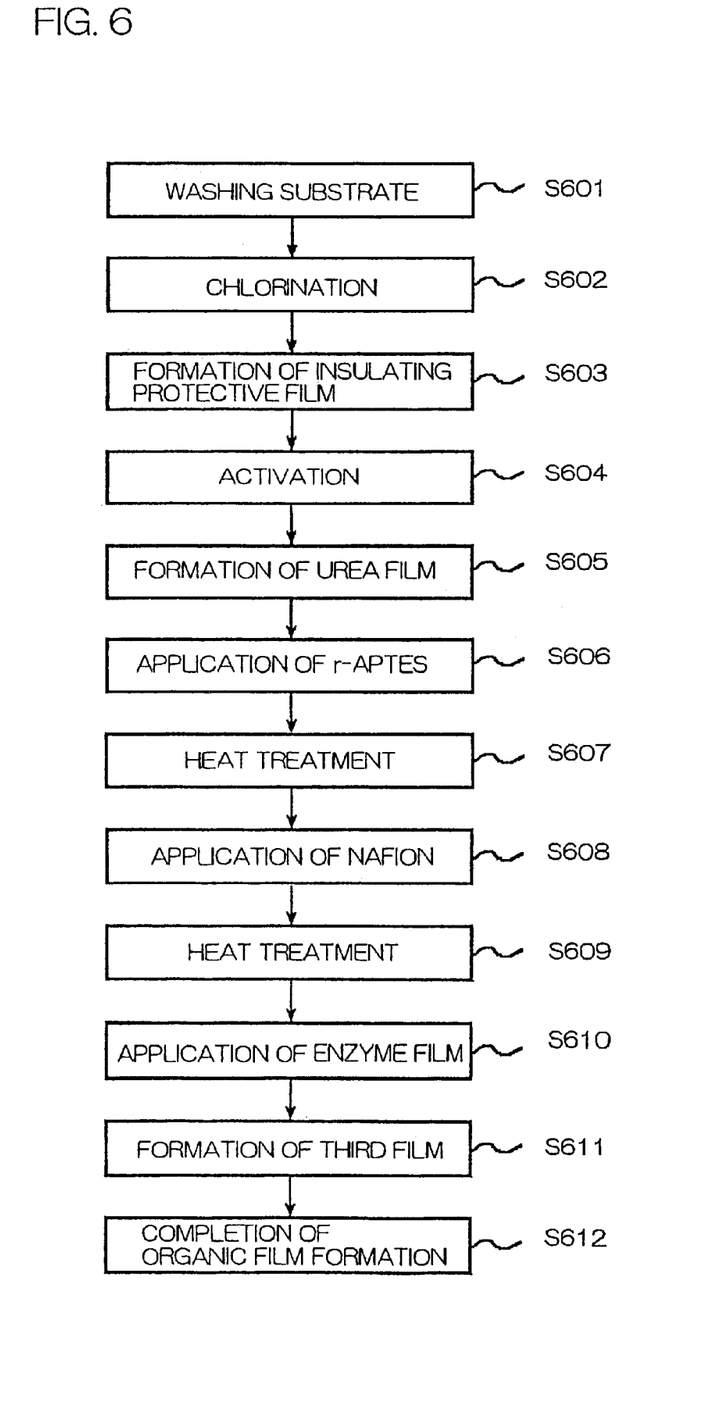
FIG. 6 is a flow chart showing respective steps of a method of fabricating an organic film.

FIG. 6 is a flow chart illustrating respective steps for forming the organic film 30. After the electrodes 24, 32 and 26 have been formed on the insulating substrate 10, the organic film 30 is formed and fixed over the insulating substrate 10.

After the substrate 10 has been washed in step 601, the silver electrode is chlorinated at a surface thereof in step 602 to thereby turn the surface into silver chloride (AgCl) in order to make the reference electrode 32. For instance, the silver electrode is dipped into a 50 mM and 25° C. solution containing $FeCl_3$ therein.

Since the reference electrode 32 gradually fuses while in operation, the reference electrode 32 acts as a parameter for determining a lifetime of the current detecting sensor. It is necessary to sufficiently densify silver chloride in order to maintain a self-potential of the reference electrode 32. The $FeCl_3$ solution has to have cleanliness. After chlorination of the silver electrode, the substrate 10 is sufficiently washed with flush water.

If the reference electrode 32 is not qualified, the resultant current detecting sensor would have unstable sensitivity-response characteristic, resulting in significant reduction in accuracy. Hence, the above-mentioned step of fabricating the reference electrode 32 is quite important.

The silver chloride layer expands, and as a result, comes to have a thickness greater than a thickness of the silver layer. However, it is preferable that the silver chloride film has a thickness equal to or smaller than 1 $\mu$m. In the instant embodiment, the silver chloride film is designed to have a thickness of 2000 angstroms.

After chlorination of the silver film, photo-sensitive polyimide resin as the insulating protective film 34 is applied entirely onto the substrate 10 in step 603. For instance, a photo-sensitive polyimide resin is spin coated onto the substrate 10 at 3000 rpm, thereby forming the insulating protective film 34 having a thickness of about 2 $\mu$m.

Then, the photo-sensitive polyimide resin is heated at 80 degrees centigrade to thereby be pre-baked, followed by exposure to light and development for patterning. Then, the photo-sensitive polyimide resin is heated at 180 degrees centigrade to thereby be post-baked.

The insulating protective film 34 is formed at least on an edge of the silver chloride film 31b, edges of the platinum and titanium films constituting the operation and opposing electrodes 24 and 26, and an edge of the platinum and titanium films constituting the electrically conductive electrode 31a. Since each of the electrodes 24, 26 and 32 has a thickness equal to or smaller than 1 $\mu$m, the insulating protective film 34 having a thickness of about 2 $\mu$m sufficiently covers the electrodes 24, 26 and 32 therewith.

By covering the edges or corners of the electrodes 24, 26 and 32 with the insulating protective film 34, even if there are generated defects in the organic film 30 to be deposited on the electrodes 24, 26 and 32, such defects will not exert harmful influence on performances of the current detecting sensor.

The insulating protective film 34 is patterned to thereby form the openings 36 and 38 above upper surfaces of the operation and opposing electrodes 24 and 26, respectively.

The insulating protective film 34 is formed at the center of the silver chloride layer with the second opening or through-hole 40. For instance, the silver chloride layer has a diameter of 0.1 mm and a thickness of about 5000 angstroms, it is preferable that the second opening 40 has a diameter in the range of 1$\mu$m to 500 $\mu$m. It is more preferable for the second opening or through-hole 40 to have a smaller diameter.

Even if the silver chloride layer is molten while the current detecting sensor is in operation, and hence, there is generated a cavity therein, it would be possible to prevent the organic film 30 from being damaged, because the silver chloride layer is supported by the insulating protective film 34.

Though the insulating protective film 34 is composed of photo-sensitive polyimide in the instant embodiment, it should be noted that a material of which the insulating protective film 34 is composed is not to be limited to photo-sensitive polyimide. For instance, the insulating protective film 34 may be comprised of a photoresist film, an inorganic insulating film such as a silicon dioxide film, or a glass insulating film.

Before depositing the organic film 30 over the platinum electrode, the electrode is activated in step 604 for enhancing adhesion and wettability. By this activation, the platinum electrode is cleaned at a surface thereof, resulting in enhancement in response sensitivity. For instance, a voltage in the range of −1.5 V to +1.5 V is applied to the platinum electrode with the platinum electrode being dipped in $Na_2SO_4$ electrolytic solution. In such condition, the platinum electrode is swept 100 times at 50 mV/s. These conditions may be determined in view of results of sensitivity, wettability and so on.

In each of steps of activating the platinum electrode, new $Na_2SO_4$ electrolytic solution is used. After activation of the platinum electrode, the product is sufficiently washed with flush water.

In order to prevent reduction in an output, caused by interfering materials contained in urine, a urea film is formed over the platinum electrode in step 605. For instance, a voltage of 0.7V is applied to the platinum electrode for ten minutes with the platinum electrode being dipped in a solution containing urea by 40 g/dl and NaCl by 150 mM. As a result, a urea film is electrochemically deposited on the platinum electrode.

The platinum electrode on which a urea film is formed would transmit a response output ½ to ⅓ smaller than a response output transmitted from a platinum electrode on which a urea film is not formed. However, the platinum electrode on which a urea film is formed can have enhanced stability in making repeated measurements.

Then, γ-APTES, a silane coupling agent, is applied onto the electrode in step 606 in order to enhance adhesion between the substrate 10 and the organic film 30.

Since the γ-APTES film is a base film in the organic film having a multi-layered structure, it is necessary for the γ-APTES film to contain no dust, and hence, have sufficient cleanliness. For instance, an aqueous solution containing γ-APTES at a concentration of 1% v/v is dropped onto the substrate 10, and is spread by spinning the substrate 10 at 3000 rpm.

In principle, γ-APTES is not bonded to a metal surface, but bonded only to a substrate surface containing silicon. However, in the instant embodiment, the γ-APTES film is formed also over the electrodes to ensure both confinement of the organic film 30 formed on the γ-APTES film, into marginal areas of the electrodes, and removal of interfering materials.

Thereafter, the product is subject to heat treatment in step 607 at 90 degrees centigrade for 10 minutes, for instance, to thereby stabilize the γ-APTES film.

In order to suppress interfering materials such as ascorbic acid and acetoaminophen, a Nafion film is formed entirely over the insulating substrate 10 in step 608. Since the Nafion film constitutes the organic film 30, the Nafion film should not contain any dusts, and should have sufficient cleanliness. In fabrication of the Nafion film, for instance, a 5% Nafion solution is dropped onto the substrate 10 by about 1.5 ml, and is spread by spinning the substrate 10 at 3000 rpm.

After application, the Nafion film is subject to heat treatment at 90 degrees centigrade for 10 minutes, for instance, for stabilization thereof in step 609.

Then, the second or enzyme film is formed over the product in step 610. The second or enzyme film determines a response characteristic to a glucose concentration in urine. If a cross-linking agent, GA, is mixed into a mixture of GOD and BSA, a cross-linking reaction makes progress, and hence, it would be difficult to form a uniform enzyme film at room temperature. Hence, it is necessary to form the second or enzyme film under optimal conditions such as a substrate temperature, a time from addition of GA until application of the enzyme film, a temperature around an applicator, revolution per minute in spin coating, revolution profile in spin coating, an amount of the mixture to be dropped, a cooling process, and a mixture ratio among GA, GOD and BSA.

If heated, an enzyme film will be deactivated. Hence, heat treatment will not be carried out after the application of the enzyme film, because heat treatment at 40 degrees centigrade or greater exerts harmful influence on enzyme reaction.

Then, the third film is formed over the product in step 611. The third film which restricts transmission therethrough of a solution containing a material to be tested is an outermost, water repellent organic film which determines linearity of the current detecting sensor, dynamic range, and readiness of washing. If the third film is thick more than needed, sensitivity of the current detecting sensor would be deteriorated, which would exert a harmful influence on response characteristic. If the third film is too thin, a sensor output is saturated at a low glucose concentration, and hence, the sensor output is not stable.

The third film is composed of perfluorocarbon or silicone, for instance.

After application of a material of which the third film is composed, the substrate is subject to a step for stabilization. However, since the enzyme film has been already formed, the step for stabilization is carried out in such a manner that the enzyme film is not deactivated. If the third film contains dust therein, restrictive transmission of the third film is deteriorated. Accordingly, the third film is necessary to have sufficient cleanliness.

Since performances of the current detecting sensor are dependent on storage conditions, temperature, humidity, atmosphere, and time, they should be optimally controlled.

For instance, the third film can be formed by spin coating at 1000 rpm. The third film is designed to have a thickness equal to or smaller than 1000 angstroms. Thereafter, the substrate is subject to heat treatment at 55 degrees centigrade for 20 minutes.

Thus, there is completed the organic film 30 in step 612.

The current detecting sensor in accordance with the second embodiment is explained hereinbelow.

Figure 7A:
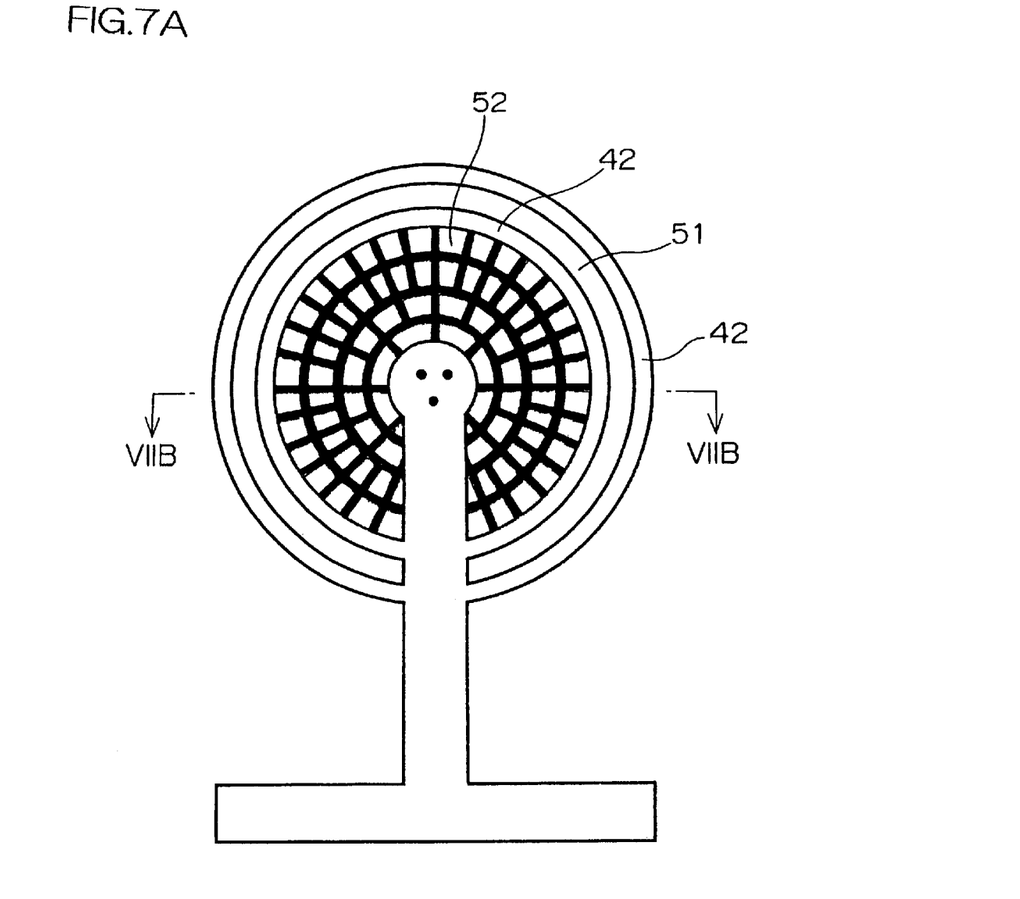
FIG. 7A is a plan view of a structure of a film constituting a sensitive section of a current detecting sensor in accordance with the second embodiment of the present invention.

In the second embodiment, the insulating protective film 34 is in the form of a mesh. The mesh-shaped insulating protective film 34 makes it possible to prevent defects having been generated in the organic film 30, from spreading.

Figure 7B:
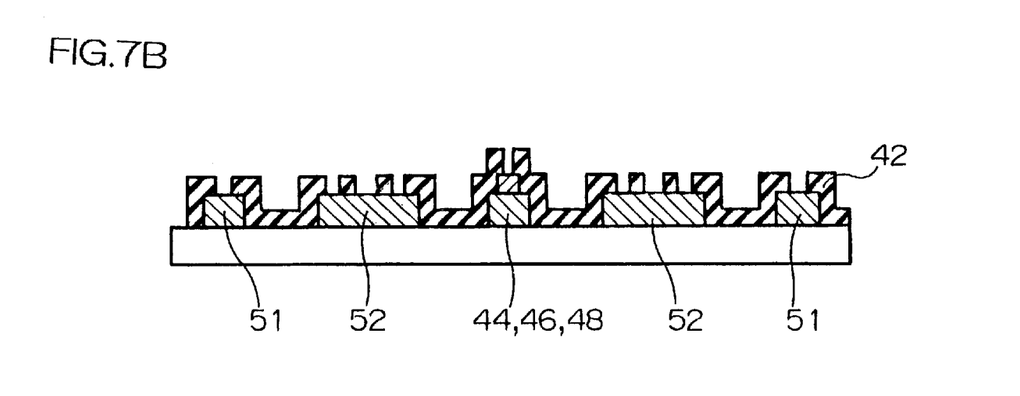
FIG. 7B is a cross-sectional view taken along the line VIIB—VIIB in FIG. 7A.
Figure 8A:
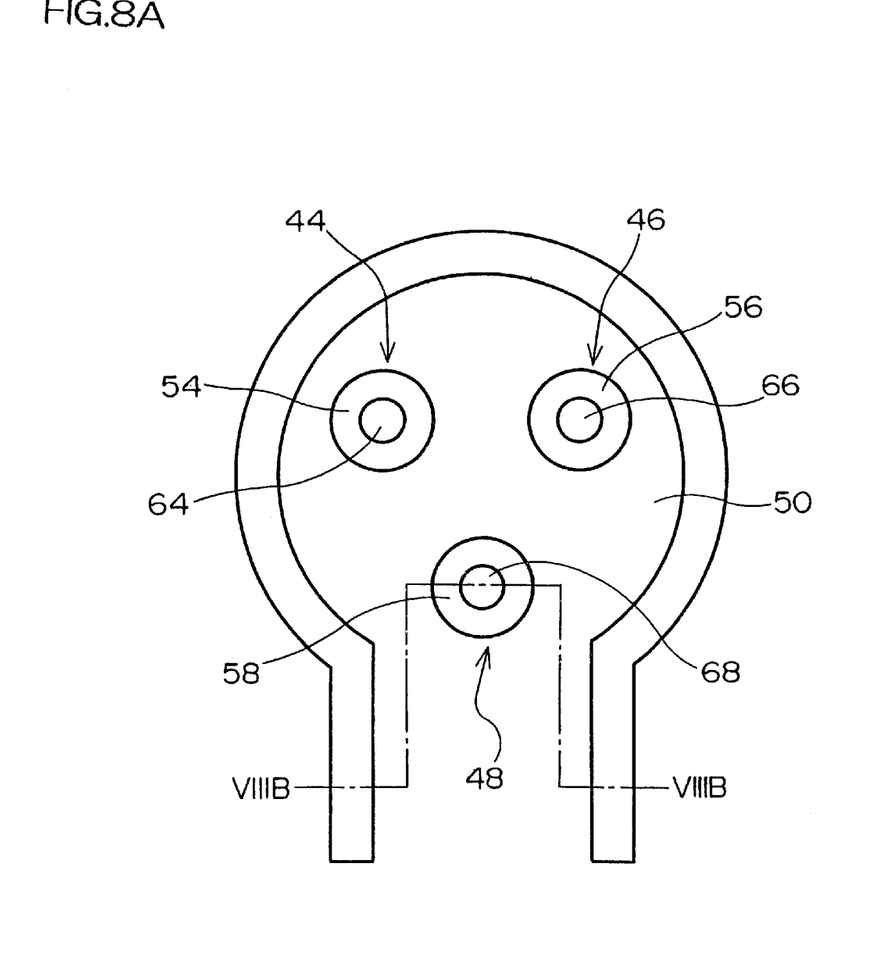
FIG. 8A is an enlarged view of a part of the film structure illustrated in FIG. 7A.
Figure 8B:
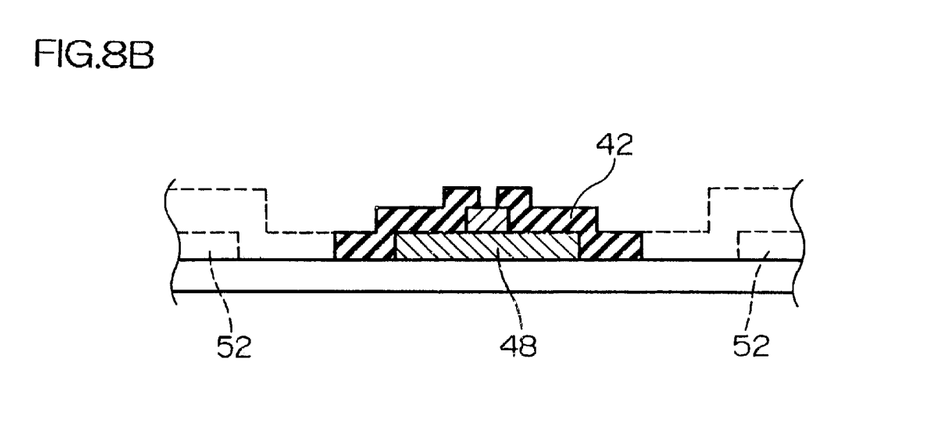
FIG. 8B is a cross-sectional view taken along the line VIIIB—VIIIB in FIG. 8A.

FIG. 7A is a plan view of a sensitive section of the current detecting sensor in accordance with the second embodiment in which the mesh-shaped insulating protective film 42 is formed on the operation electrode 24, and FIG. 7B is a cross-sectional view taken along the line VIIB—VIIB in FIG. 7A. FIG. 8A is an enlarged view of reference electrodes of the current detecting sensor illustrated in FIG. 7A, and FIG. 8B is a cross-sectional view taken along the line VIIIB—VIIIB in FIG. 8A.

As illustrated in FIG. 8A, the current detecting sensor in accordance with the second embodiment is designed to include three reference electrodes 44, 46 and 48. The reference electrodes 44, 46 and 48 are surrounded by an operation electrode 52, as illustrated in FIG. 7B. The reference electrode 52 is surrounded by an opposing electrode 51, as illustrated in FIG. 7B.

As illustrated in FIG. 8A, three AgCl island patterns 54, 56 and 58 are formed on a platinum layer 50. These AgCl island patterns 54, 56 and 58 are covered with the insulating protective film 42, and the insulating protective film 42 is formed with second openings or through-holes 64, 66 and 68 so as to expose a portion of upper surfaces of the AgCl island patterns 54, 56 and 58.

As illustrated in FIG. 7A, the mesh-shaped insulating protective film 42 includes a plurality of almost rectangular openings 52 radially arranged around the reference electrodes 44, 46 and 48. The platinum layer exposed in each of the openings 52 constitutes the operation electrode 52.

The mesh-shaped insulating protective film 42 is covered with an organic film (not illustrated). That is, the rectangular openings 52 are all filled with the organic film.

Figure 9:
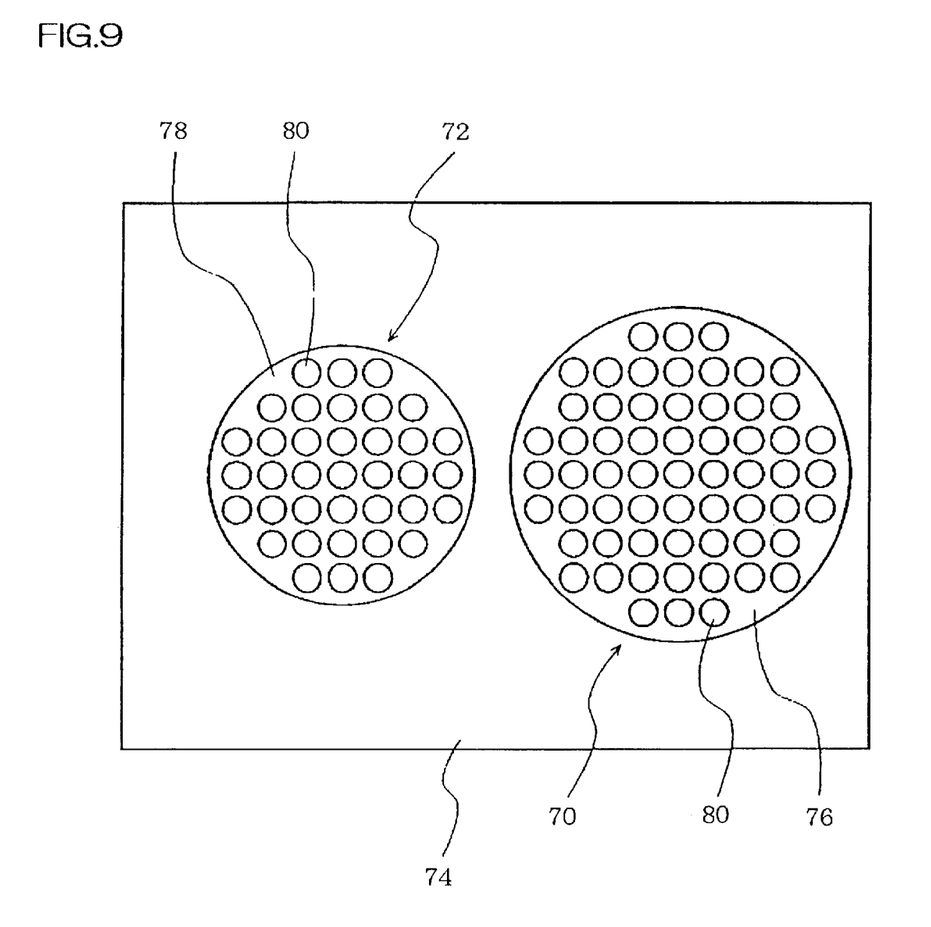
FIG. 9 is a plan view illustrating an example of a mesh-shaped insulating protective film.

FIG. 9 illustrates another example of a mesh-shaped insulating protective film.

As illustrated in FIG. 9, an insulating protective film 74 is in the form of a mesh on both operation electrode 70 and opposing electrode 72. Specifically, the insulating protective film 74 is designed to have a plurality of circular openings 80 arranged in a matrix on both a platinum layer 76 constituting the operation electrode 70 and a platinum layer 78 constituting an opposing electrode 72.

A shape of openings formed in the insulating protective film is not to be limited to a rectangle as illustrated in FIG. 7A and a circle as illustrated in FIG. 9. The insulating protective film may be designed to have openings in any shape.

In the above-mentioned embodiments, a multi-layered structure of Ag/Pt/Ti films is formed in a thin film structure. However, the multi-layered structure may be formed in a thick film structure.

While the present invention has been described in connection with the preferred embodiments, the invention provides many advantages as follows.

First, it is possible to prevent peeling off of an organic film which would be caused by fusion of a silver chloride film and poor coverage on edges of electrodes. As a result, there can be obtained stable response characteristic.

Secondly, the current detecting sensor in accordance with the present invention can have a longer lifetime than conventional sensors.

Thirdly, the current detecting sensor in accordance with the present invention makes it possible to stabilize a self-potential of reference electrodes.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Application No. 10-86215 filed on Mar, 31, 1998 including specification, claims, drawings and summary is incorporated herein by reference in its entirety.

What is claimed is:

1. A current detecting sensor comprising:
   (a) an insulating substrate;
   (b) a first electrode formed on said insulating substrate, said first electrode comprising an electrically conductive electrode and a metal layer formed on said electrically conductive electrode, said metal layer having a smaller area than a are a of said electrically conductive electrode;

(c) a second electrode formed on said insulating substrate;

(d) a third electrode formed on said insulating substrate;

(e) an insulating protective film covering said insulating substrate therewith and further covering at least edges of said first, second and third electrodes therewith, said insulating protective film being formed with first, second and third openings at upper surfaces of said first, second and third electrodes, respectively; and (f) an organic film covering said first to third electrodes and said insulating protective film therewith.

2. The current detecting sensor as set forth in claim 1, wherein said metal layer has a two-layered structure.

3. The current detecting sensor as set forth in claim 2, wherein said two-layered structure includes a silver (Ag) layer and a silver chloride (AgCl) layer formed on said silver layer.

4. The current detecting sensor as set forth in claim 1, wherein said electrically conductive electrode has a multi-layered structure.

5. The current detecting sensor as set forth in claim 4, wherein said multi-layered structure includes a platinum (Pt) layer and a titanium (Ti) layer formed on said platinum layer.

6. The current detecting sensor as set forth in claim 4, wherein said multi-layered structure includes a silver (Ag) layer, a platinum (Pt) layer, and a titanium (Ti) layer deposited in this order.

7. The current detecting sensor as set forth in claim 1, wherein said first opening has a smaller diameter than diameters of said second and third openings.

8. The current detecting sensor as set forth in claim 1, wherein said first opening has a diameter in the range of 1 $\mu$m to 500 $\mu$m both inclusive.

9. The current detecting sensor as set forth in claim 1, wherein said insulating protective film has a thickness equal to or greater than thicknesses of said first, second and third electrodes.

10. The current detecting sensor as set forth in claim 1, wherein said insulating protective film is in the form of a mesh, and said second and third openings are comprised of a plurality of fine openings.

11. The current detecting sensor as set forth in claim 1, wherein said insulating substrate is composed of a material selected from a group consisting of glass, ceramic, polyimide and glass epoxy, and wherein said insulating protective film is composed of a material selected from a group consisting of photoresist, polyimide resin, solder resist, epoxy resin, phenol resin, silicon dioxide, and glass.

12. The current detecting sensor as set forth in claim 1, wherein said organic film is comprised of:

a first film for restricting transmission of a solution containing a material to be tested, therethrough;

a second film to which enzyme is fixated; and a third film for removing an interfering material contained in said solution.

13. The current detecting sensor as set forth in claim 12, wherein said first film is composed of a material selected from a group consisting of perfluorocarbon and silicone, said second film is composed of a mixture of glucose oxidase (GOD), bull serum albumin (BSA), and glutaric aldehyde (GA), and said third film is composed of $\gamma$-aminopropyltrietoxysilane and ionomer fluoride.

14. A current detecting sensor comprising:

(a) an insulating substrate;

(b) a first electrode formed on said insulating substrate, said first electrode comprising an electrically conductive electrode and a plurality of metal islands formed on said electrically conductive electrode, said metal islands each having a smaller area than a area of said electrically conductive electrode;

(c) a second electrode formed on said insulating substrate, said second electrode surrounding said first electrode therewith;

(d) a third electrode formed on said insulating substrate;

(e) an insulating protective film covering said insulating substrate therewith and further covering at least edges of said first, second and third electrodes therewith, said insulating protective film being formed with first, second and third openings at upper surfaces of said first, second and third electrodes, respectively; and (f) an organic film covering said first to third electrodes and said insulating protective film therewith.

15. The current detecting sensor as set forth in claim 14, wherein said third electrode surrounds said second electrode therewith.

16. The current detecting sensor as set forth in claim 14, wherein said metal layer has a two-layered structure.

17. The current detecting sensor as set forth in claim 16, wherein said two-layered structure includes a silver (Ag) layer and a silver chloride (AgCl) layer formed on said silver layer.

18. The current detecting sensor as set forth in claim 14, wherein said electrically conductive electrode has a multi-layered structure.

19. The current detecting sensor as set forth in claim 18, wherein said multi-layered structure includes a platinum (Pt) layer and a titanium (Ti) layer formed on said platinum layer.

20. The current detecting sensor as set forth in claim 18, wherein said multi-layered structure includes a silver (Ag) layer, a platinum (Pt) layer and a titanium (Ti) layer deposited in this order.

21. The current detecting sensor as set forth in claim 14, wherein said first opening has a smaller diameter than diameters of said second and third openings.

22. The current detecting sensor as set forth in claim 14, wherein said first opening has a diameter in the range of 1 $\mu$m to 500 $\mu$m both inclusive.

23. The current detecting sensor as set forth in claim 14, wherein said insulating protective film has a thickness equal to or greater than thicknesses of said first, second and third electrodes.

24. The current detecting sensor as set forth in claim 14, wherein said insulating protective film is in the form of a mesh, and said second and third openings are comprised of a plurality of fine openings.

25. The current detecting sensor as set forth in claim 14, wherein said insulating substrate is composed of a material selected from a group consisting of glass, ceramic, polyimide and glass epoxy, and wherein said insulating protective film is composed of a material selected from a group consisting of photoresist, polyimide resin, solder resist, epoxy resin, phenol resin, silicon dioxide, and glass.

26. The current detecting sensor as set forth in claim 14, wherein said organic film is comprised of:

a first film for restricting transmission of a solution containing a material to be tested, therethrough;

a second film to which enzyme is fixated; and a third film for removing an interfering material contained in said solution.

27. The current detecting sensor as set forth in claim 26, wherein said first film is composed of a material selected from a group consisting of perfluorocarbon and silicone, said second film is composed of a mixture of glucose oxidase (GOD), bull serum albumin (BSA), and glutaric aldehyde (GA), and said third film is composed of γ-aminopropyltrietoxysilane and ionomer fluoride.

28. A method of fabricating a current detecting sensor, comprising the steps of:

(a) forming first to third electrodes on a substrate, said first electrode being comprised of an electrically conductive electrode and a metal layer formed on said electrically conductive electrode, said metal layer having a smaller area than a area of said electrically conductive electrode, said second electrode being comprised of an electrically conductive electrode, said third electrode being comprised of an electrically conductive electrode;

(b) depositing an insulating protective film over a product resulting from said step (a);

(c) patterning said insulating protective film in such a manner that said insulating protective film covers said substrate therewith and further covers at least edges of said first, second and third electrodes therewith, and that said insulating protective film has first, second and third openings at upper surfaces of said first, second and third electrodes, respectively; and (d) covering a product resulting from said step (c) with an organic film.

29. The method as set forth in claim 28, wherein said metal layer is comprised of a silver (Ag) layer and a silver chloride (AgCl) layer formed on said silver layer, said method further comprising the step of chlorinating said silver layer to thereby turn said silver layer at a surface thereof into said silver chloride layer.

30. The method as set forth in claim 28, wherein said first opening is formed in said step (c) so as to have a smaller diameter than diameters of said second and third openings.

31. The method as set forth in claim 28, wherein said insulating protective film is patterned in said step (c) into a mesh, and said second and third openings are formed of a plurality of fine openings.

32. The method as set forth in claim 28, wherein said insulating protective film is deposited in said step (b) in such a manner that said insulating protective film has a thickness equal to or greater than thicknesses of said first, second and third electrodes.

33. A method of fabricating a current detecting sensor, comprising the steps of:

(a) forming first to third electrodes on a substrate, said first electrode being comprised of an electrically conductive electrode and a plurality of metal islands formed on said electrically conductive electrode, said metal islands each having a smaller area than a area of said electrically conductive electrode, said second electrode being comprised of an electrically conductive electrode, said third electrode being comprised of an electrically conductive electrode, said second electrode surrounding said first electrode therewith;

(b) depositing an insulating protective film over a product resulting from said step (a);

(c) patterning said insulating protective film in such a manner that said insulating protective film covers said substrate therewith and further covers at least edges of said first, second and third electrodes therewith, and that said insulating protective film has first, second and third openings at upper surfaces of said first, second and third electrodes, respectively; and (d) covering a product resulting from said step (c) with an organic film.

34. The method as set forth in claim 33, wherein each of said metal islands is comprised of a silver (Ag) layer and a silver chloride (AgCl) layer formed on said silver layer, said method further comprising the step of chlorinating said silver layer to thereby turn said silver layer at a surface thereof into said silver chloride layer.

35. The method as set forth in claim 33, wherein said first opening is formed in said step (c) so as to have a smaller diameter than diameters of said second and third openings.

36. The method as set forth in claim 33, wherein said insulating protective film is patterned in said step (c) into a mesh, and said second and third openings are formed of a plurality of fine openings.

37. The method as set forth in claim 33, wherein said insulating protective film is deposited in said step (b) in such a manner that said insulating protective film has a thickness equal to or greater than thicknesses of said first, second and third electrodes.

* * * * *